United States Patent [19]

Rascher et al.

[11] Patent Number: 5,595,749
[45] Date of Patent: Jan. 21, 1997

[54] INSECTICIDE COMPOSITION AND PROCESS FOR MAKING SAME

[75] Inventors: Lawrence Rascher, Wayne; Samir Bishai, Iselin; William Perlberg, Franklin Lakes, all of N.J.

[73] Assignee: The Hartz Mountain Corporation, Secaucus, N.J.

[21] Appl. No.: 417,809

[22] Filed: Apr. 6, 1995

[51] Int. Cl.$^6$ .................................................. A01N 25/06
[52] U.S. Cl. ........................ 424/405; 424/403; 424/488; 424/45
[58] Field of Search ..................................... 424/401, 403, 424/405, 488, DIG. 10, 45

[56] References Cited

U.S. PATENT DOCUMENTS

| | | |
|---|---|---|
| 3,102,842 | 9/1963 | Phillips et al. . |
| 3,944,662 | 3/1976 | Miller, Jr. et al. . |
| 4,900,551 | 2/1990 | Ohtsubo et al. .................. 424/402 |
| 4,954,529 | 9/1990 | Koch et al. ...................... 514/594 |

FOREIGN PATENT DOCUMENTS

| | | |
|---|---|---|
| 1040553 | 5/1964 | United Kingdom . |
| 1425127 | 4/1973 | United Kingdom . |

*Primary Examiner*—Thurman K. Page
*Assistant Examiner*—Sharon Howard
*Attorney, Agent, or Firm*—Kuhn and Muller

[57] ABSTRACT

An insecticide spray is provided with a water insoluble organophosphate ester (tetrachlorvinphos) that is emulsified in an aqueous carrier and may be delivered via a pump or aerosol to kill fleas and ticks, including the deer tick, on household pets such as cats and dogs.

10 Claims, No Drawings

INSECTICIDE COMPOSITION AND PROCESS FOR MAKING SAME

BACKGROUND OF THE INVENTION

Tetrachlorvinphos, sold under the trade name of Rabon®, is an organophosphate insecticide first synthesized commercially by Shell Chemical in the USA during 1969 for agricultural use only.

Prior art includes the use of Rabon® in plastic flea collars, powders, and aerosol sprays in which the Rabon® in the aerosol spray is solubilized in an organic (non-aqueous) phase that is anhydrous. However, there are no known emulsified systems that solubilize Rabon® in water without deceomposition of Rabon®.

SUMMARY OF THE INVENTION

The present invention relates to an insecticide composition containing a water insoluble organophosphate ester insecticide, such as Rabon® (tetrachlorvinphos), that is emulsified in an aqueous carrier which may be delivered via a pump or aerosol spray device to kill fleas and ticks, including the deer tick, on household pets such as cats and dogs.

Tetrachlorvinphos (Rabon®) is an anhydrous insecticide that rapidly decomposes in the presence of water. In the present invention the use of an oil in water emulsion effectively precludes the decomposition of the insecticide and maintains the integrity of the active constituent by surrounding the tetrachlorvinphos molecule with a hydrophobic matrix.

The insecticide spray composition of the present invention has a reduced hydrocarbon content that reduces its flammability and produces a more environmentally-friendly product.

The insecticide spray composition of the present invention has a reduced hydrocarbon content that reduces the volatile organic compounds (VOC[5]) that affect government Clean Air Quality standards. The active insecticide component emulsified in an aqueous base reduces flammability and warehouse storage liability. Furthermore, the product of the present invention is more environmentally friendly.

DESCRIPTION OF THE PRESENT INVENTION

Tetrachlorvinphos [2-chloro-1-(2,4,5-trichlorophenyl) vinyl dimethyl phosphate] is an insecticide that is a member of the class of organophosphate esters. It is a crystalline water insoluble solid, white to faintly yellow with a characteristic odor. The preferred concentration of the insecticide component is in the range of 0.9% to 1.3%, depending upon formulation for a pump spray or aerosol.

Esters of straight chain carboxylic acids, especially diesters of dicarboxylic acids, such as diisopropyl adipate or dibutyl adipate and triesters of tricarboxylic acids, such as citric acid, are especially effective in solubilizing and emulsifying tetrachlorvinphos (TCVP). A ratio of of ester to TCVP of at least about 12:1, preferably about 17:1 is generally required to stabilize TCVP. The upper limit of ester to TCVP has not been critical.

Propylene glycol ceteth-3-acetate is a member of the broad class of general compounds used in the cosmetic industry identified as non-ionic surfactants which exhibit surfactant properties and may be used as emulsifiers. This surfactant is an example and is not meant to be limiting. The formulation delivery system type, such as pump spray or by aerosol spray, dictates the preferred ratio.

Hydrocolloids are used to maintain the formulation as a dispersion. These hydrocolloids may be selected from the group of water soluble polysaccharides, such as alginates, xanthan gum, guar gum, locust beam gum, methylcellulose including chemical derivatives, and are not intended to be limited to such. Alginates are preferred with a concentration range of 0.05 to 0.30% with 0.20% the concentration of choice for the formulation.

Fragrances and preservatives may be added as required.

The present invention is further illustrated by the following examples, which is not intended to be limiting:

Example I (Pump Spray)

This example provides a detailed description of the process of the invention identifying the components that are contained within each phase of the process and the general sequential incorporation of the phases.

To a vessel of sufficient capacity to accommodate all ingredients, the following materials are charged at 70°–90° F.; deionized water (80.65%) and hydrocolloid and silicate complex (0.60%). The hydrocolloid and silicate complex are preblended and added to the water using an eductor. The eductor is connected to a water tank and a pump is used for delivering an appropriate flow rate that is sufficient to quickly draw the hydrocolloid mixture down the funnel into the water stream. The mixture is homogenized until a solution which is homogeneous and lump free is formed.

To another kettle of sufficient capacity, the following materials are charged at 70°–90° F. in the order of addition noted. Diisopropyl Adipate (16.50%), Propylene Glycol Ceteth-3-Acetate (0.5%), Fragrance (0.10%), and Rabon® (1.10%). The mixture is mixed until the Rabon® is completely dissolved.

The oil phase from above is added to the water phase of the first mixture with stirring and homogenization and the batch may be heated to 130° F. The heat is then turned off and the batch is allowed to cool. Preservative is added as required to the batch as soon as cooling begins. pH adjustment is required and sodium hydroxide is added to raise the pH to 7.5. Mixing and homogenizing the batch is continued for several hours. The batch is filtered through a 100 micron filter before filling dispensing containers. Filling may be accomplished through the use of any acceptable filling machine into bottle sizes of choice.

Example II (Aerosol)

This example provides a description of the process and the components that are contained within each phase of the process and the general sequential incorporation of the phases.

To a kettle of sufficient capacity, the following materials are charged at 70°–90° F.; deionized water (75%), and hydrocolloid and silicate complex (preblended powders) (0.40%). The hydrocolloid and silicate complex are added to the water using an eductor, and the mixture is mixed at high speed with homogenization until the solution is homogeneous and lump free. To another kettle, the following raw materials are charged at 70°–90° F. in order. Diisopropyl adipate (19%), Propylene Glycol Ceteth-3-Acetate (4%), Fragrance (0.13%), Rabon® (1.5%), and mixed until the Rabon® is dissolved.

The oil phase from above is added to the water phase and is mixed at high speed with homogenization until homogeneous.

Preservative is added to the emulsion as required and mixed until homogeneous. A pH adjustment is required to raise pH to 7.3–7.6. Mixing and homogenizing and filtering, the batch is continued through a cartridge or bag type filter (75 microns) before filling. During the filling process, the batch is vigorously stirred (no homogenization) at all times while in the holding tanks. The formulation is filled into appropriate aerosol cans using a propellant, such as dimethyl ether and isobutane-propane, that are common state-of-the-art propellants. In this aerosol spray embodiment, the concentrate percentage is 75%. and the propellant is 25%.

TEST RESULTS COMPARING THE PREFERRED EMBODIMENTS WITH PRIOR ART

The following examples of developmental formulas of pump sprays (266/25/1, 266/34/1) demonstrates that unemulsified Rabon® solubilized in large volumes of alcohol to which water is added is non-stable and deteriorates as compared to formulas (1361/30/1, 1331/81/1) in which the Rabon® molecule is entrapped in a hydrophobic micelle formed by esters of carboxylic acids which are especially resistant to hydrolysis.

|  | N.B. # 1361/30/1 | N.B. # 1331/81/1 | N.B. # 266/25/1 | N.B. # 266/34/1 |
|---|---|---|---|---|
| Chemicals (%) | | | | |
| Rabon | 1.1 | 1.1 | 2.05 | 1.02 |
| Deionized Water | 80.8 | 56.2 | 42.85 | 46.38 |
| Propylene Glycol | 0.5 | 3.0 | — | — |
| Ceteth-3-Acetate | | | | |
| Diisopropyl Adipate | 16.5 | 14.0 | — | — |
| Magnesium Aluminum Silicate | 0.4 | 0.2 | — | — |
| Xanthan Gum | 0.2 | 0.1 | — | — |
| Fragrance | 0.1 | 0.1 | 0.10 | 0.10 |
| Glydant | 0.4 | 0.3 | — | — |
| Propellant | — | 25.0 | — | — |
| Ethoxylated Lauryl Alcohol | — | — | 5.00 | — |
| Isopropanol | — | — | 50.00 | 49.00 |
| Ethoxylated Oleyl Alcohol | — | — | — | 3.00 |
| Potassium Phosphate (dibasic) | — | — | — | 0.50 |
| Rabon® Stability (%) | | | | |
| Theoretical | 1.078 | 1.078 | 2.009 | 1.000 |
| Initial | 1.049 | 1.092 | 2.00 | 1.030 |
| RT 3 Mos. | 1.054 | 1.079 | — | — |
| 110° F. 3 Mos. | 1.054 | 1.075 | — | — |
| 130° F. 1 Mos. | 1.057 | 1.090 | 1.17 (14 days) | 0.400 (17 days) |

It is noted that other modifications may be made to the present invention, without departing from the scope of the invention, as noted in the appended claims.

What is claimed is:

1. An insecticide composition suitable for dispensing by spraying, comprising an effective amount of tetrachlorvinphos, a water insoluble, hydrolysis prone organophosphate ester insecticide dissolved in an emulsifiable hydrophobic micelle formed by esters of carboxylic acids, said insecticide component being emulsified in an aqueous carrier.

2. The composition of claim 1, wherein said emulsifiable hydrophobic micelle comprises esters of straight chain carboxylic acids.

3. The composition of claim 1 wherein said emulsifiable hydrophobic micelle comprises diesters of dicarboxylic acid or triesters of tricarboxylic acids.

4. The composition of claim 1, wherein said emulsifiable hydrophobic micelle is present in an amount of at least 12 parts to 1 part of said insecticide component.

5. The composition of claim 1, further comprising a non-ionic emulsifying agent.

6. The composition of claim 1 further comprising a hydrocolloid agent and silicate complex in an amount sufficient to maintain the stability.

7. The composition of claim 6 wherein said hydrocolloid and silicate complex are selected from the group consisting of water, clay, soluble polysaccharides and a mixture thereof.

8. An apparatus for dispensing the composition of claim 1 wherein said dispensing apparatus is an aerosol spray.

9. An apparatus for dispensing the composition of claim 1 wherein said dispensing apparatus is a pump spray.

10. A composition of claim 1 wherein said composition is delivered as a dip formula.

* * * * *

UNITED STATES PATENT AND TRADEMARK OFFICE
CERTIFICATE OF CORRECTION

PATENT NO. : 5,595,749
DATED : January 21, 1997
INVENTOR(S) : Rascher et al

It is certified that error appears in the above—identified patent and that said Letters Patent is hereby corrected as shown below:

On the title page: Item [75]

Inventors: Lawrence Rascher, Wayne, NJ
Samir Bishai, Iselin, NJ
William Perlberg, Franklin Lakes, NJ
Richard Glass, Allentown, PA Signed and Sealed this Twenty-ninth Day of April, 1997

Attest:

BRUCE LEHMAN

Attesting Officer

Commissioner of Patents and Trademarks